(12) United States Patent
Carrara

(10) Patent No.: US 9,439,575 B2
(45) Date of Patent: Sep. 13, 2016

(54) METHOD FOR ACQUIRING AND PROCESSING HEART RATE DATA

(71) Applicant: Marco Carrara, San Felice (IT)

(72) Inventor: Marco Carrara, San Felice (IT)

(*) Notice: Subject to any disclaimer, the term of this patent is extended or adjusted under 35 U.S.C. 154(b) by 0 days.

(21) Appl. No.: 14/759,664

(22) PCT Filed: Jan. 9, 2014

(86) PCT No.: PCT/EP2014/050336
§ 371 (c)(1),
(2) Date: Jul. 8, 2015

(87) PCT Pub. No.: WO2014/108481
PCT Pub. Date: Jul. 17, 2014

(65) Prior Publication Data
US 2015/0342482 A1 Dec. 3, 2015

(30) Foreign Application Priority Data
Jan. 10, 2013 (IT) .............................. MI2013A0024

(51) Int. Cl.
*A61B 5/02* (2006.01)
*A61B 5/024* (2006.01)
(Continued)

(52) U.S. Cl.
CPC ......... *A61B 5/02438* (2013.01); *A61B 5/6803* (2013.01); *A61B 5/7271* (2013.01);
(Continued)

(58) Field of Classification Search
CPC .......... A61B 5/05085; A61B 5/02438; A61B 5/0603; A61B 5/7271; A61B 5/742; A61B 5/746; A61B 5/7475; G02C 11/10; G02C 7/10

USPC ............. 600/509, 382; 607/139–141; 351/41
See application file for complete search history.

(56) References Cited

U.S. PATENT DOCUMENTS 6,431,705 B1 8/2002 Linden
2007/0109491 A1 5/2007 Howell et al.
(Continued)

FOREIGN PATENT DOCUMENTS

IT MI20101083 A1 12/2011

OTHER PUBLICATIONS

International Search Report dated Apr. 30, 2014; International Application No. PCT/EP2014/050336; International Filing Date: Jan. 9, 2014; 3 pages.
(Continued)

*Primary Examiner* — Paula J Stice
(74) *Attorney, Agent, or Firm* — Blank Rome LLP

(57) ABSTRACT

Acquiring and processing heart rate data involves providing glasses having a microcontroller, a heart rate sensor positionable to a user, a configuration memory, at least one data memory, a clock/calendar electronic circuit, a visual and/or audible signaling unit, a rechargeable autonomous electrical power supply, and one switch for the heart rate detection function. The method involves providing a programming and data transfer unit external to the glasses, providing a connection system between the glasses and the external programming and data transfer unit, programming the configuration memory (102) of the glasses using the external programming and data transfer unit, with a minimum heart rate threshold value, a maximum heart rate threshold value, and a heart rate reading frequency value, acquiring readings in data memory of the glasses during activity, processing an alarm signal when a detected heart rate value is above a maximum or below a minimum.

11 Claims, 6 Drawing Sheets

(51) Int. Cl.
*A61B 5/00* (2006.01)
*G02C 11/00* (2006.01)

(52) U.S. Cl.
CPC .............. *A61B 5/742* (2013.01); *A61B 5/746* (2013.01); *A61B 5/7475* (2013.01); *G02C 11/10* (2013.01); *A61B 2560/0214* (2013.01)

(56) References Cited

U.S. PATENT DOCUMENTS

2010/0098278 A1* 4/2010 Sorensen ............. H04R 25/554
    381/323
2013/0041590 A1* 2/2013 Burich ................ G06F 19/3418
    702/19
2013/0294969 A1* 11/2013 Chen ........................ A61L 2/10
    422/28

OTHER PUBLICATIONS

Written Opinion dated Apr. 30, 2014; International Application No. PCT/EP2014/050336; International Filing Date: Jan. 9, 2014; 6 pages.

* cited by examiner

METHOD FOR ACQUIRING AND PROCESSING HEART RATE DATA

FIELD OF USE

The present invention refers to a method for acquiring and processing heart rate data.

BACKGROUND OF THE INVENTION

It is very important to monitor, especially during a prolonged physical effort, at least some of the main vital parameters of a person, as one of his anomalies can be symptomatic of a dysfunction or pathology on a coronary and/or cardiovascular, and/or more generally a circulatory level.

Some of such pathologies are silent and asymptomatic and only their early and timely diagnosis can contribute to avoid the worst, which sometimes means the onset of permanent damage and sometimes even death.

SUMMARY OF THE INVENTION

The use of glasses has been proposed having a sensor of the heart rate.

Such glasses, in addition to the function to which they are normally assigned, are per se limited only to provide to the wearer an indication of the detected heart rate. Therefore, the technical task of the present invention is to provide an extremely convenient, practical and efficient method for acquiring and processing heart rate data.

Another aim of the invention is to realize a method for acquiring and processing heart rate data by means of special glasses, which permits to greatly expand the minimum functionalities and proposes intended for the method itself.

The technical task, and also these and other aims, according to the present invention, are reached with a method for acquiring and processing heart rate data, characterized in that it comprises the steps of:

Providing at least one pair of glasses comprising a microcontroller, at least one heart rate sensor positioned against an anatomic area of a user, at least one configuration memory, at least one data memory, a clock/calendar electronic circuit, at least one visual and/or audible signalling unit, at least one rechargeable autonomous electrical power supply source, and at least one switch for at least switching on/off the heart rate detection function.

Providing at least one programming and data transfer unit external to the glasses Providing at least one connection system between said glasses and said external programming and data transfer unit Programming the configuration memory of the glasses, by means of said external programming and data transfer unit, with at least a minimum heart rate threshold value, a maximum heart rate threshold value, and a heart rate reading frequency value Acquiring a plurality of readings in the data memory of the glasses during an activity in which the user wears the glasses, wherein each reading comprises a detected heart rate value and the corresponding time of detection Processing, in real time daring said activity, by means of the visual and/or audible signalling unit, at least one alarm signal when the current reading comprises a detected heart rate value that is not below the maximum heart rate threshold or not above the minimum heart rate threshold.

Preferably the programming and data transfer unit in turn comprises a controller to which a data input unit for the user, a data output unit for the user, an electrical power supply source and a data memory are connected.

Preferably according to the method of the invention, after the conclusion of said activity by the user, a step of connecting said glasses to said programming and data transfer unit by means of said connection system is made, by means of the connection system, wherein the readings acquired during said activity are stored in said data memory of the programming and data transfer unit, and the autonomous electrical power supply source is recharged by electrical power supply source of the programming and data transfer unit.

Preferably, the connection system is wired, but the method according to the invention does not exclude the adoption of a wireless connection system between said glasses and said programming and data transfer unit.

Preferably, the recharging of said autonomous electrical power supply source of the glasses and the storing of the readings in the data memory of said programming and data transfer unit occur simultaneously.

Preferably, according to the method of the invention, a graphical processing step is provided, wherein on the output device of said programming and data transfer unit, paths are shown in a comparative or alternative form, processed from the said programming and data transfer unit and showing for the user's activities the corresponding readings performed.

Preferably, according to the method of the invention, a step of loading various user profiles into said data memory of said programming and data transfer and is provided, each user profile comprising corresponding minimum and maximum threshold heart rate and reading frequency values, and a programming step of the configuration memory of the glasses with a profile selected from said programming and data transfer unit.

According to the method of the invention, a profile program, wherein the minimum and maximum threshold heart rate values be variable during the acquisition time of the heart rate, is also possible.

BRIEF DESCRIPTION OF THE DRAWINGS

Further features and advantages of the invention will be more evident from the description of a preferred but non exclusive embodiment of the acquisition and data processing of heart rate data according to the finding, shown in an indicative and non limitative way in the annexed drawings, in which.

DETAILED DESCRIPTION OF THE ILLUSTRATED EMBODIMENTS

Figure 1:
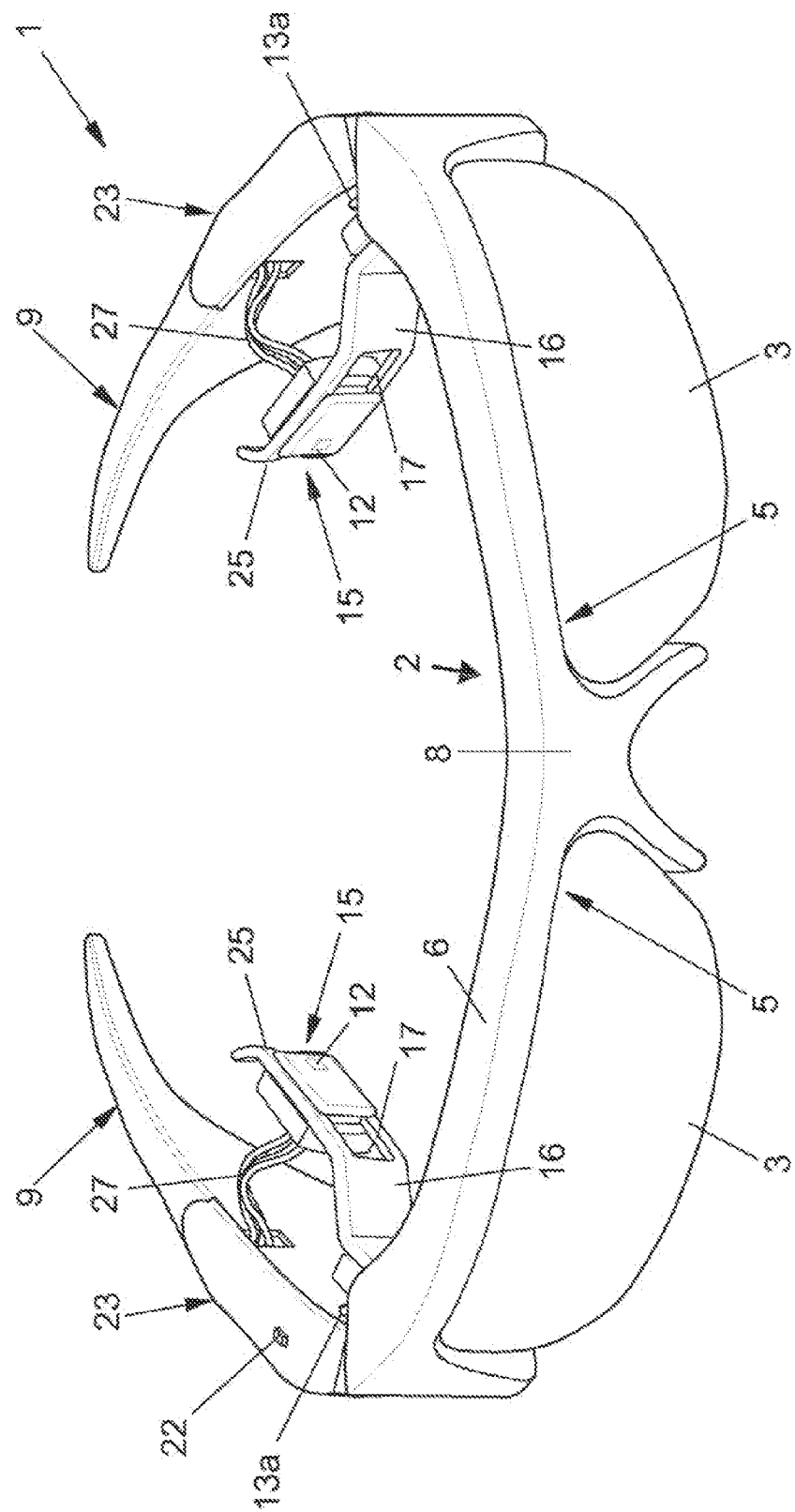
FIG. 1 shows a view of a preferred embodiment of glasses used in the method.
Figure 2:
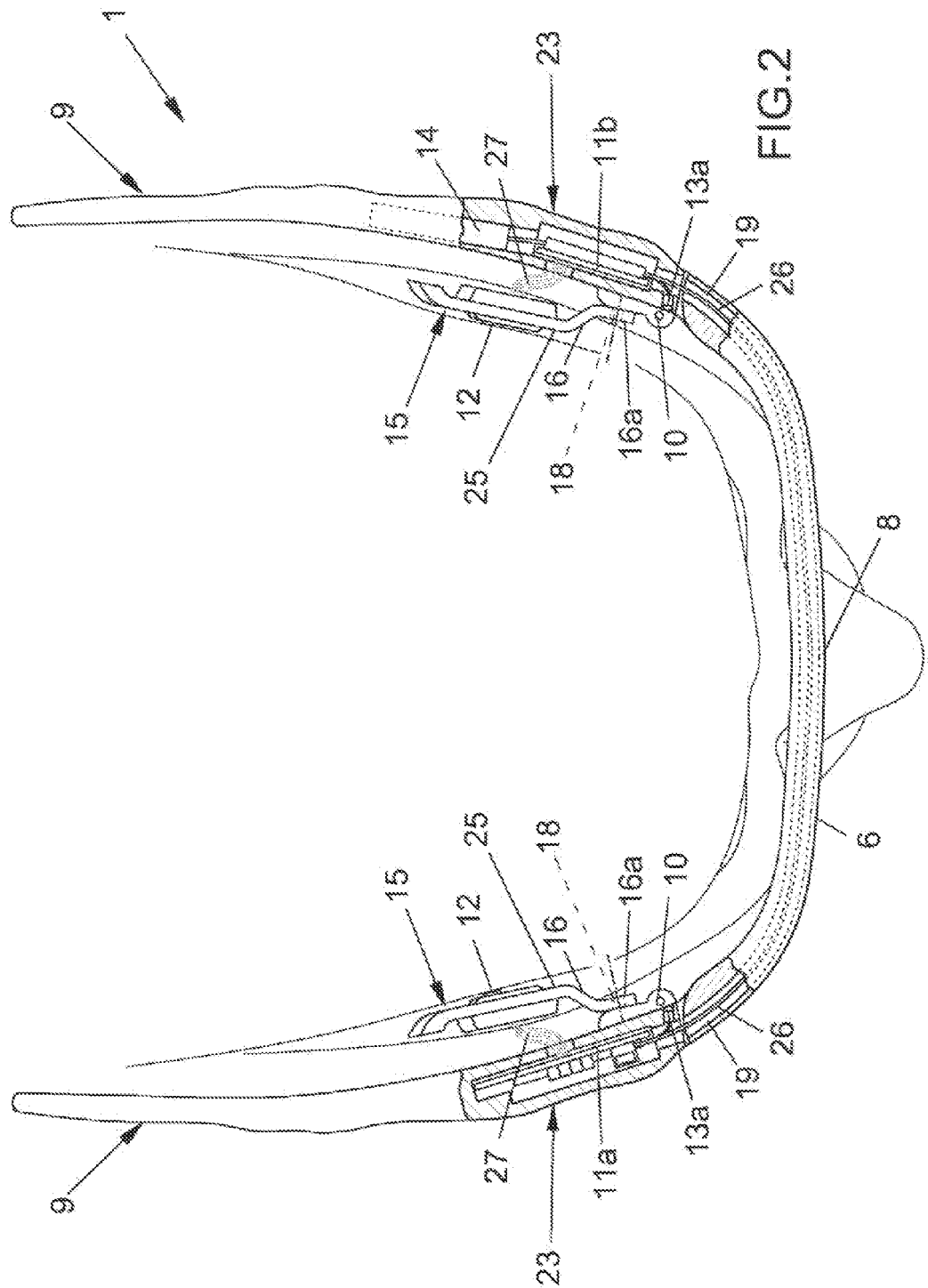
FIG. 2 shows a top plan view of the glasses on the wearer, with a cross-section of the frame in the hinged areas of front temple pieces.
Figure 3:
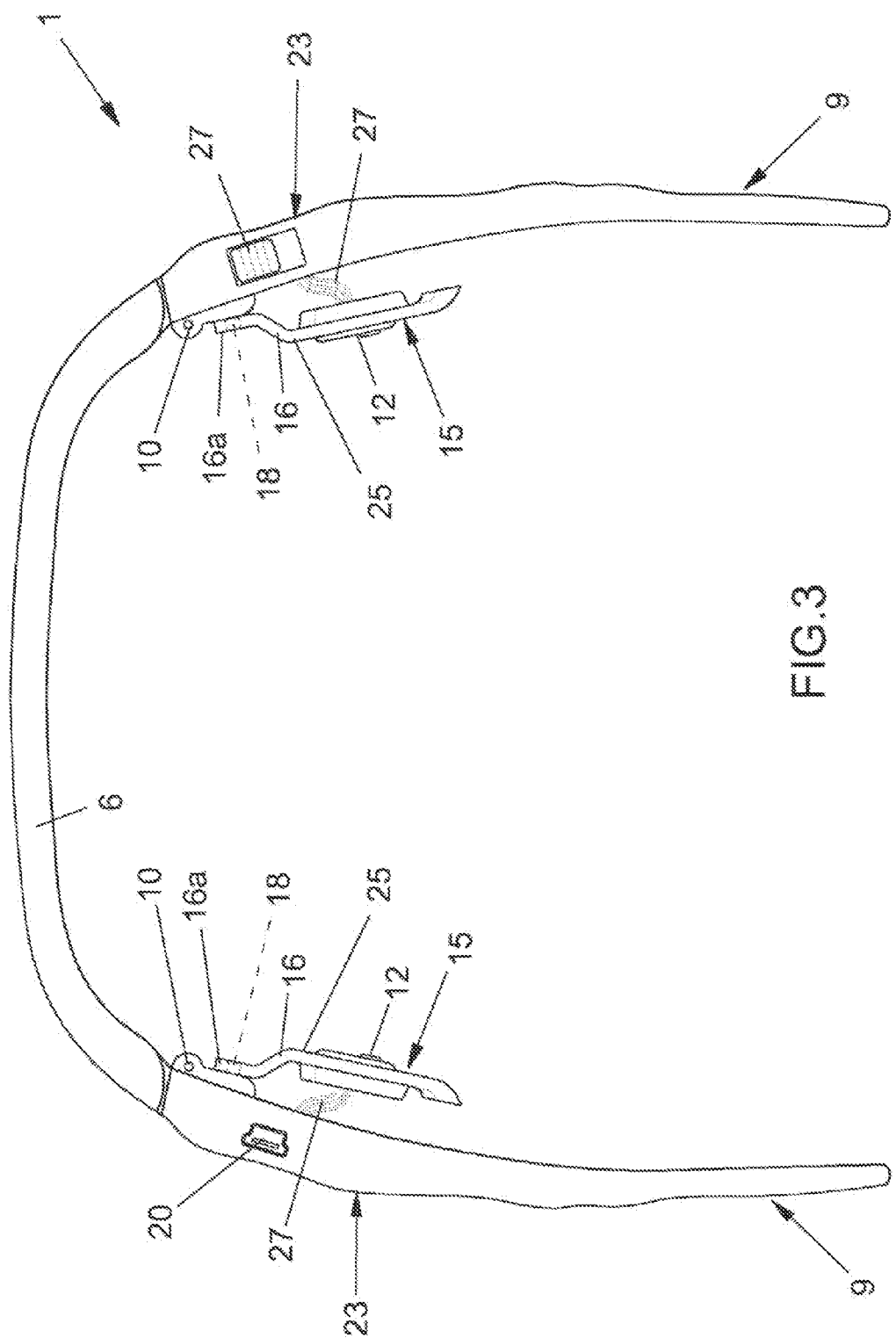
FIG. 3 shows a top plan view of the glasses.
Figure 4:
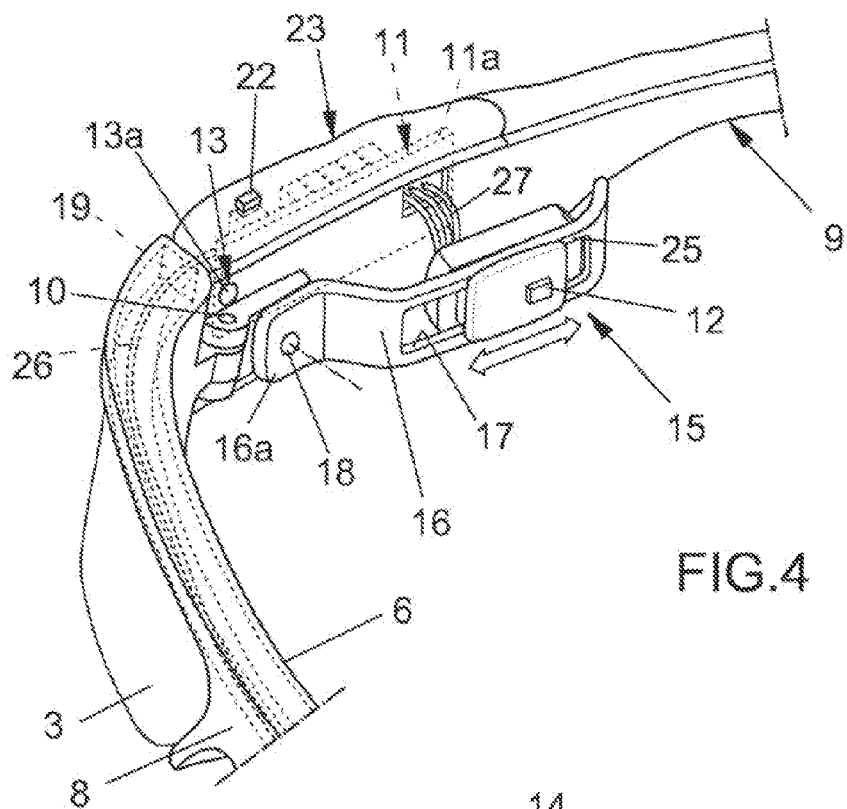
FIG. 4 shows in detail the frame in the hinged area between the right temple piece and the front of the frame, wherein an arrow shows the translation direction for regulating the linear position of the sensor along the support element.
Figure 5:
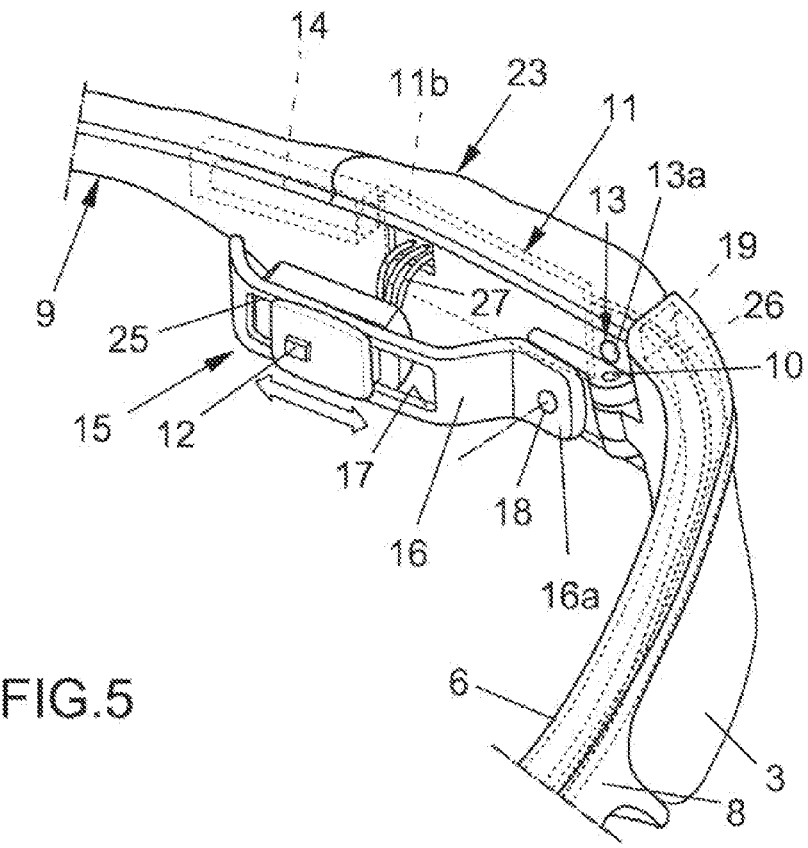
FIG. 5 shows in detail the frame in the hinged area between the left temple piece and the front of the frame, wherein an arrow shows the translation direction for regulating the linear position of the sensor along the support element.
Figure 6:
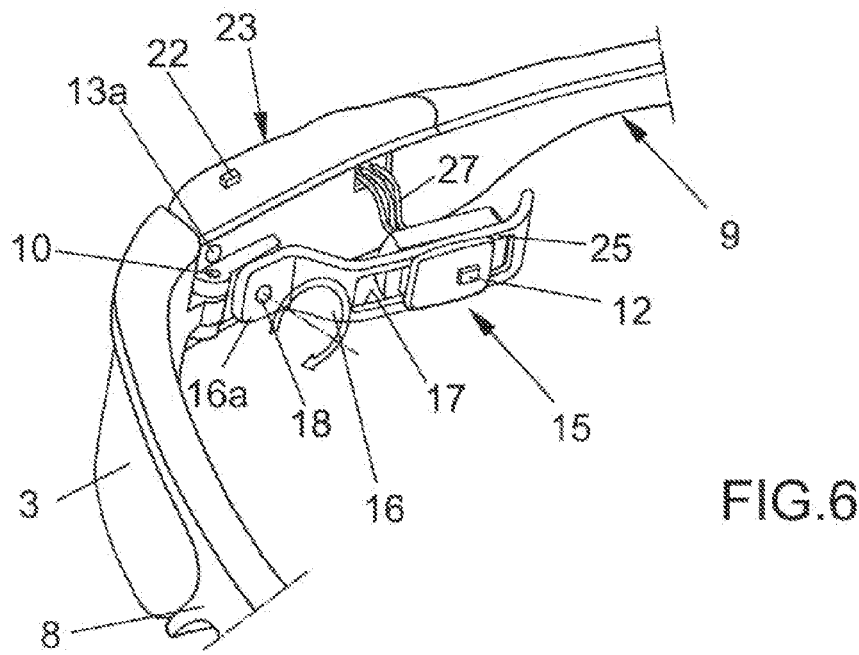
FIGS. 6 and 7 show in detail the name in the hinged area between the right temple piece and the front of the frame, wherein an arrow shows the regulation of the angular position of the support element of the sensor.
Figure 7:
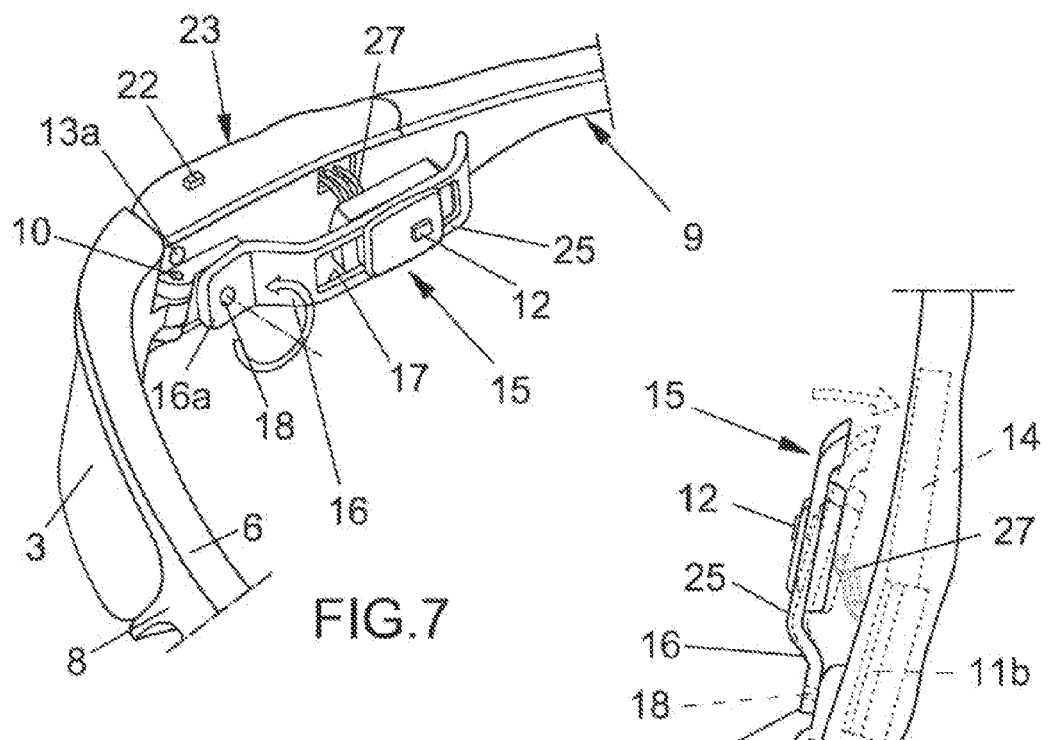
Figure 8:
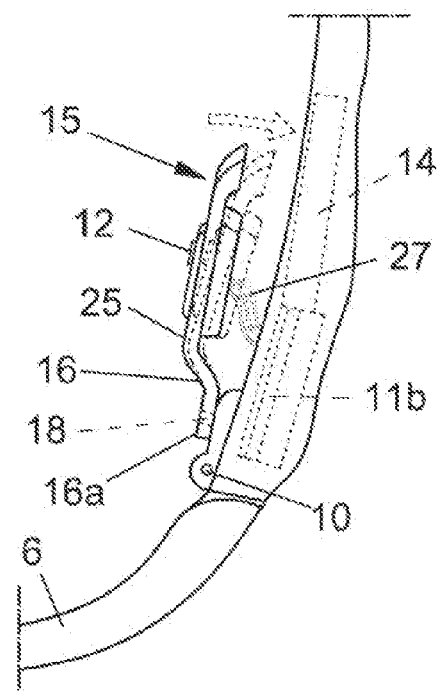
FIG. 8 shows in detail the frame in the hinged area between the left temple piece and the front of the frame, wherein an arrow shows the flexion to which the support element of the sensor can be subject, shown with a continuous line in a rest position and with a dotted line in a flexed position, taken when the glasses are worn, FIG. 9 schematically shows the architecture of the parts concurring to the execution of the method.
Figure 9:
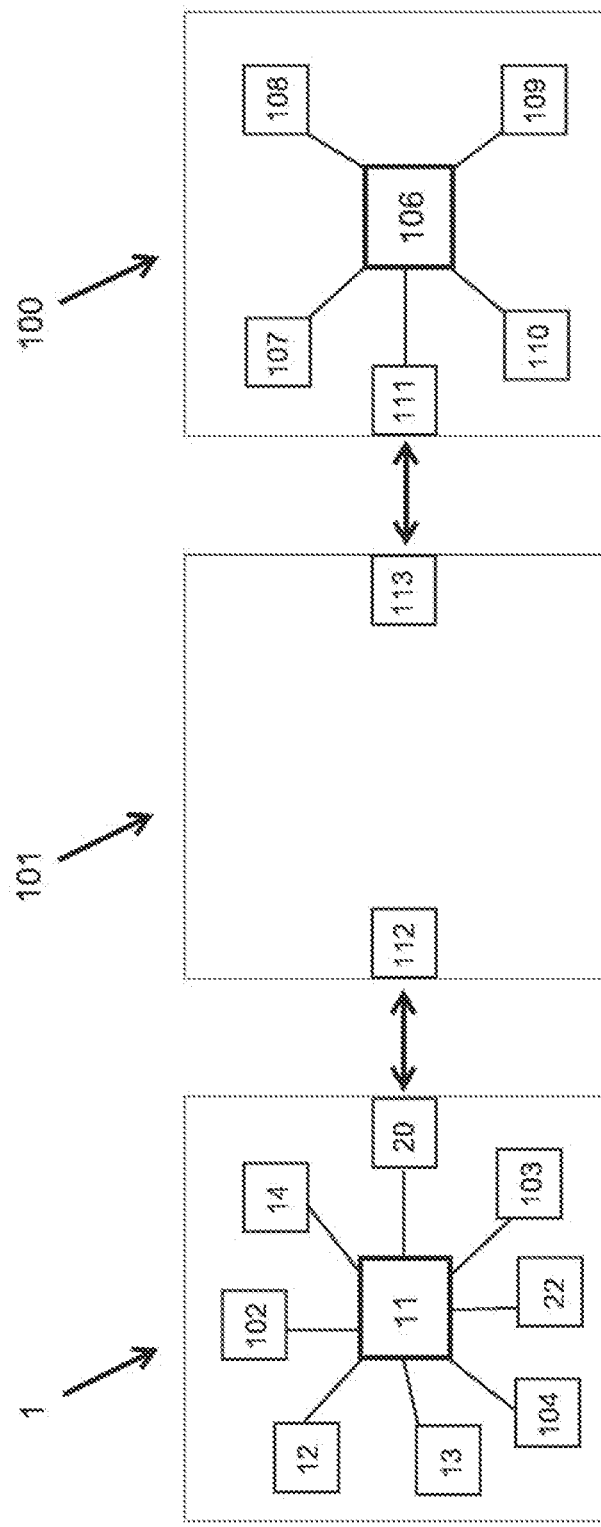

With reference to the cited figures, the method of acquiring and processing heart rate data uses at least one pair of glasses 1, at least one programming and data transfer unit 100 separated and external to the glasses 1, and at least one connection system 101 between the programming and data transfer unit 100 and the glasses 1.

The glasses 1 comprise a microcontroller 11 to which one or more heart rate sensors 12 are connected, which can be positioned against an anatomic area of a user and suitable for the detection of the heart rate, a configuration memory 102, a data memory 103, a clock/calendar electronic circuit 104, a visual and/or audible signalling unit 13, and a rechargeable autonomous electrical power supply source 14, for example a battery.

To the controller 11 also at least one interface port 20 is connected, for example a USB port, by which the glasses 1 can be connected with the connection system 101.

The glasses 1 further comprise a switch 22 for starting/stopping at least some of their functions, and in particular at least the heart rate detection function.

The external programming and data transfer unit 100 has a controller 106 to which a data memory 107, an input unit 108 for the user, an output unit 109 for the user, and an electrical power supply source 110 are connected.

The programming and data transfer unit 100 comprises a resident software suitably dedicated for interfacing the glasses 1 and processing the transferred data.

The input unit 108 for the user can be for example a push-board, a keypad, a keyboard, a touch-screen.

The output unit 109 for the user can be for example a display, a screen, a touch-screen.

The electrical power supply source 110 can be for example a battery or a power supply connected to the mains.

The programming and data trans for unit 100 finally comprises at least one interface port 111, for example one USB port, with which it can be connected to the connection system 101.

The programming and data transfer unit 100 can alternatively take the form of a proprietary unit, a personal computer (desktop or laptop), a computer tablet or a smart phone with a suitable computational and memory capacity.

The connection system 101 can comprise for example a multi-core cable equipped with a connector 112 for the connection to the interface port 20 with the glasses 1 and a connector 113 for the connection to the interface port 111 of the programming and data transfer unit 100.

The user who intends to monitor the heart rate during the execution of a certain physical activity, for example a sports racing, first must plan the configuration memory 102 present in the glasses 1 by setting an user profile comprising a minimum threshold heart rate, a maximum threshold heart rate, and a rate value or reading frequency value.

The setting of the user profile can be made thanks to the input unit 108 of the programming and data transfer unit 100, to which the glasses 1 must be connected through the connection system 101.

Advantageously, through the input unit 108 various user profiles can be loaded in the data memory 107 of the programming and data transfer unit 100, each profile comprising corresponding minimum and maximum threshold heart rate and reading frequency values.

More precisely, the user connects the glasses 1 to the programming and data transfer unit 100 through the connection system 101, and performs through the input unit 108, the selection of the user profile which he like most. The controller 106 acquires the selection and controls the transfer of the profile acquired from said data memory 107 of the programming and data transfer unit 100 to the configuration memory 102 of the glasses 1.

If the configuration memory 102 is initially empty the configuration values referring to the minimum and maximum heart rate and reading frequency threshold are written; if on the contrary the configuration memory 102 is not empty, having a previous program, the present configuration values are overwritten on the previous ones so to update them.

The configuration memory 102 is also programmed with the current date and time data, in order to adjust calendar and clock so that the readings which will be performed thereafter be referred to the precise date-hour time.

After programming or reprogramming the configuration memory 102, the user disconnects the glasses 1 from the programming and data transfer unit 100, wearing them in order to perform the physical activity which must be monitored. During the physical activity the microcontroller 11, following the sampling rate corresponding to the selected profile, controls the execution of a series of readings of the heart rate and through the electronic circuit of clock-calendar 104, associates to each detected heart rate value the corresponding detection time.

The microcontroller 11 controls the storage of the readings with the corresponding time of occurrence in the data memory 103, present in the glasses 1.

The readings are therefore organized as tables of pairs of date-hour values and of detected heart rate and the tables in turn can be organized in multiple sessions, corresponding to different drive cycles front the user of the switch 22. Advantageously, the microcontroller 11 controls the visual and/or audible signalling unit in order to process in real time outing the performance of the physical activity of the user, at least one alarm signal when the current reading comprises a value of detected heart rate not lower than the maximum set heart rate threshold or not greater than the minimum set heart rate threshold.

After the conclusion of the physical activity the user connects the glasses 1 to the external programming and data transfer unit 100 through the connection system 101. At this point the controller 106 controls the transfer of the readings acquired daring the physical activity of the data memory 103 of the glasses 1 to the data memory 107 of the programming and data transfer unit 100, and also controls the transfer of electrical energy from the electrical supply source 110 of the programming and data transfer unit 100 to the autonomous electrical supply source 14 of the glasses 1 for reloading it. These two steps can be also performed at the same time.

Advantageously, the controller 106 of the programming and data transfer unit 100 uses the readings stored in the memory 107 in order to process and visualize on the output device 109 some paths in a comparative or alternative form, which reproduce for the activities of the user the corresponding readings performed.

Reference is made now more in detail to a preferred construction for the glasses 1 winch can be used in the method for acquiring and processing heart rate data of the present invention. The glasses 1 as seen comprise the switch 22 which is advantageously miniaturized and serves for starting/stopping in particular the function of acquiring the heart rate but also the function of generating the alarm signal.

The switch 22 can also serve for starting/stopping other functions among which for example there is the function of programming the configuration memory of the glasses, the data transfer function and the energy recharging function. Apart from that, for starting/stopping the function of heart rate detection, the starting/stopping of all other functions cannot be necessarily controlled by the user 22, but from the connection/disconnection itself between glasses 1 and programming and data transfer unit 100, through the connection system 101.

The frame 2 has a front 5 equipped with two open circles 6, a connecting bridge 8 among the circles 6, and temple pieces 9 connected through a respective hinge 10 to the front 5.

The temple pieces 9 have a box-like enlargement 23 at their portion proximal to the front 5 of the frame 2.

The microcontroller 11 for ergonomic reasons is made of two distinct electronic cards 11a and 11b.

The visual and/or audible signalling unit 13 for the generation of a light signal correlated to the detected heart rate preferably comprises one or more LEDs 13a, whereas for the generation of an audible signal correlated to the detected heart rate, it preferably comprises one or more buzzers (not shown).

The glasses 1 have adjustable means for a stable positioning of the sensor 12 against the anatomical area destined to the detection of the heart rate.

The positioning means comprise in particular at least one support element 15 for the sensor 12.

The support element 15 has an elastic flexible longitudinal body which is hinged to a temple pieces 9 of the frame 2.

The support element 15 is made in particular of a longitudinal plate 16 providing at least one longitudinal plan portion 25 and which, at its longitudinal end 16a proximal to the front 5 of the frame 2, is hinged through a pin 18 to the temple piece 9 and is placed with one of its main faces at a short distance facing the inner face of the box-like portion 23 of the temple piece 9.

The pin 18 is so oriented to permit an oscillation of the plate 16 in its main lying plane substantially parallel to the inner face of the box-like portion 23 of the temple piece 9.

The sensor 12 is supported along a translation guide 17 made from the body of the support element 15.

More precisely the translation guide 17 is developed in the longitudinal direction of the support element 15.

The precise regulation of the angular and linear position of the sensor 12 can be made by providing a friction coupling between the support element 15 and the temple piece 9 through the pin 18, and a friction coupling between the sensor 12 and the support element 15 through the translation guide 17. In practice for the precise regulation of the angular position of the sensor 12, it is sufficient to manually apply on the support element 15 a rotational force greater than the friction force which maintains the support element integrated with the temple piece 9, whereas for the precise regulation of the linear position of the sensor 12 it is sufficient to manually apply on the sensor 12 a translation force greater than the friction force which maintains the sensor 12 integrated with the support element 15.

Once having placed the sensor 12 against the anatomical detection area, the elastic flexion to which the support element is subjected due to the interference with the head of the wearer, generates the friction force necessary for maintaining the sensor 12 integrated with the anatomical detection area in any situation, either when the wearer is not active or when he is performing a physical activity of some importance.

The glasses 1 are provided with a second sensor 12 carried by a second support element 15 associated to the opposed temple piece 9.

The second support element 15 is structurally and functionally equal to the first one.

Also the second sensor 12 is structurally and functionally equal to the first one. The autonomous electrical power supply source 14 and the microcontroller 11 are housed in special seats provided in the frame 2 and in particular in the box-like enlarged portion 23 of the temple piece 9.

The electrical cables 26 for connecting the autonomous electrical power supply source 14 to the microcontroller 11 are developed along the temple pieces 9, the bridge 8 and the upper arc of the circles 6 of the front 5 of the frame 2.

In particular the frame 2 has a duct 19 for the passage of the electrical cables 26. The electrical cables 27 for connecting the sensor 12 to the microcontroller 11 instead can be developed in the space between the support element 15 and the inner face of the box-like enlarged portion 23 of the temple piece 9.

The method for acquiring and processing heart rate data according to the invention provides for the possibility, through the data processing software installed in the programming and data transfer unit 100, of a series of operating modes, among which: the creation of graphs visualizing the paths showing the downloaded data of heart rate readings, in function of the time (date-hour) with visual indication of the events of possible overcoming of the threshold values, as explained before; the creation and managing of the user profiles in order to program the glasses 1 in different modes according to the user and to visualize the corresponding paths in a comparative or alternative form, as explained before; the possibility of integrating and combining the reading paths with data coming from other devices, for example a GPS navigator, an altimeter, maps or plans of the territory; the possibility of statistically processing the data, obtain metrics, make comparisons among different users or session of the same user; the possibility of storing in a data memory data and sessions also separated for different user profiles; and the possibility of remotely sharing the data, statistical information integrated among different users. Therefore a series of possibilities and extensions of the minimum functionalities is likely to occur, if the connection of the unit 100 in turn with other external devices is realized, through cabled or wireless connection means. The connection could be an Internet connection.

All this connects and integrates the world of Social Networking. The method for acquiring and processing heart rate data so conceived is suitable for various changes and variations, all within the scope of the inventive concept; furthermore all details can be substituted with technical equivalent elements.

The invention claimed is:

1. A method for acquiring and processing heart rate data, the method comprising the steps of:
providing at least one pair of glasses comprising a microcontroller, at least one heart rate sensor positionable against an anatomic area of a user, at least one configuration memory, at least one data memory, a clock/calendar electronic circuit, at least one visual and/or audible signaling unit, at least one rechargeable autonomous electrical power supply source, and at least one switch for at least switching an on/off heart rate detection function;
providing at least one programming and data transfer unit external to the glasses;
providing at least one connection system between the glasses and the external programming and data transfer unit;
programming the configuration memory of the glasses, by use of the external programming and data transfer unit, with at least a minimum heart rate threshold value, a maximum heart rate threshold value, and a heart rate reading frequency value;
loading various user profiles into a data memory of the external programming and data transfer unit, each user profile comprising corresponding minimum heart rate threshold value, maximum heart rate threshold value and heart rate reading frequency value, wherein the method further comprises a selection phase in which, when the glasses are connected to the external programming and data transfer unit, a user selects a profile via the data input unit of the external programming and data transfer unit, and the controller of the external programming and data transfer unit programs the configuration memory of the glasses with the selected profile;
acquiring a plurality of readings in the data memory of the glasses, during an activity in which a user wears the glasses, wherein each reading comprises a detected heart rate value and a corresponding time of detection; and
processing, in real time during said activity, by use of the visual and/or audible signaling unit, at least one alarm signal when a current reading involves a detected heart rate value not below the maximum heart rate threshold, or not above the minimum heart rate threshold.

2. The method of claim 1, wherein the external programming and data transfer unit comprises a controller communicating with a data input unit for a user, a data output unit for the user, an electrical power supply source, and a data memory.

3. The method of claim 2, further comprising the step, after completion of the activity, of connecting the glasses to the external programming and data transfer unit, by use of the connection system, wherein the controller of the external programming and data transfer unit commands a transfer of readings acquired during the activity in the data memory of the glasses into data memory of the external programming and data transfer unit, and commands a transfer of electricity from the electrical power supply source of the external programming and data transfer unit to the autonomous electrical power supply source of the glasses.

4. The method of claim 3, wherein recharging the autonomous electrical power supply source of the glasses, and memorization of readings in the data memory of the external programming and data transfer unit occur simultaneously.

5. The method of claim 2, further comprising a processing and display step, where the controller of the external programming and data transfer unit processes and displays, on the output device of the external programming and data transfer unit, graphs in a comparative or alternative form showing corresponding readings recorded for a user's activities.

6. The method of claim 5, further comprising the steps of:
accessing data originating from other devices, including at least one of a GPS navigator, an altimeter, maps or plans of a territory, data of different users, data of different sessions of a same user, and
integrating and combining the graphs with the data originating from the other devices.

7. The method of claim 5, further comprising the step of statistically analyzing the readings recorded for the user's activities.

8. The method of claim 5, further comprising the step of remotely sharing readings originating from various external programming and data transfer units.

9. The method of claim 1, wherein the glasses comprise an adjustment device for stably positioning the sensor against the anatomic area of the user.

10. The method of claim 9, wherein the adjustment device comprises at least one support element for the at least one heart rate sensor, the at least one support element having an elastically flexible body.

11. The method of claim 10, wherein the at least one heart rate sensor is slidingly supported by the at least one support element, which is in turn hinged to a temple piece of a frame of the glasses.

* * * * *